US006631989B2

(12) United States Patent
Odom et al.

(10) Patent No.: US 6,631,989 B2
(45) Date of Patent: *Oct. 14, 2003

(54) NON-INVASIVE OCULAR ASSESSMENT METHOD AND ASSOCIATED APPARATUS

(75) Inventors: James V. Odom, Morgantown, WV (US); James E. Smith, Bruceton Mills, WV (US); Robert P. M. Craven, Cookeville, TN (US)

(73) Assignee: West Virginia University, Morgantown, WV (US)

( * ) Notice: Subject to any disclaimer, the term of this patent is extended or adjusted under 35 U.S.C. 154(b) by 80 days.

This patent is subject to a terminal disclaimer.

(21) Appl. No.: 09/932,750

(22) Filed: Aug. 17, 2001

(65) Prior Publication Data

US 2002/0171805 A1 Nov. 21, 2002

Related U.S. Application Data

(63) Continuation-in-part of application No. 09/860,241, filed on May 18, 2001.

(51) Int. Cl.[7] .................................................. A61B 3/10
(52) U.S. Cl. ....................................... 351/205; 351/246
(58) Field of Search ................................. 351/200, 205, 351/206, 209, 210, 213, 221, 246; 600/407, 318–321, 558; 180/272; 340/500, 576

(56) References Cited

U.S. PATENT DOCUMENTS

| | | | | |
|---|---|---|---|---|
| 4,334,738 A | * | 6/1982 | Seckinger | 351/246 |
| 4,995,716 A | | 2/1991 | Warnicki et al. | |
| 5,129,400 A | * | 7/1992 | Makino et al. | 351/206 |
| 5,159,361 A | | 10/1992 | Cambier et al. | |
| 5,297,554 A | * | 3/1994 | Glynn et al. | 351/206 |
| 5,308,919 A | * | 5/1994 | Minnich | 351/221 |
| 5,422,690 A | * | 6/1995 | Rothberg et al. | 351/209 |
| 5,666,953 A | * | 9/1997 | Wilk | 600/407 |
| 5,684,561 A | * | 11/1997 | Yancey | 351/209 |
| 5,729,619 A | * | 3/1998 | Puma | 382/115 |
| 6,120,460 A | * | 9/2000 | Abreu | 600/558 |
| 6,285,505 B1 | * | 9/2001 | Melville et al. | 351/206 |
| 6,442,410 B1 | * | 8/2002 | Steffes | 600/319 |
| 2002/0024633 A1 | * | 2/2002 | Kim et al. | 351/206 |

* cited by examiner

*Primary Examiner*—George Manuel
*Assistant Examiner*—John R. Sanders
(74) *Attorney, Agent, or Firm*—Arnold B. Silverman; Eckert Seamans Cherin & Mellott, LLC

(57) ABSTRACT

A method of monitoring a subject for medical conditions includes causing light to impinge on at least one eye of the subject, directing reflected light from such light beam to photosensors, converting the received reflected light to corresponding electrical signals which are delivered to a processor. Processing the signals by effecting a comparison between stored information regarding the medical condition and the data provided by the monitoring to determine if an undesired medical condition exists and, if so, communicating such result. The cycle is repeated at predetermined intervals which may be short or prolonged. The stored information may be information relating to the specific subject or general information regarding normal and abnormal conditions of the eye representative of toxicity. The eyes may be monitored sequentially or simultaneously. Related apparatus is provided.

35 Claims, 7 Drawing Sheets

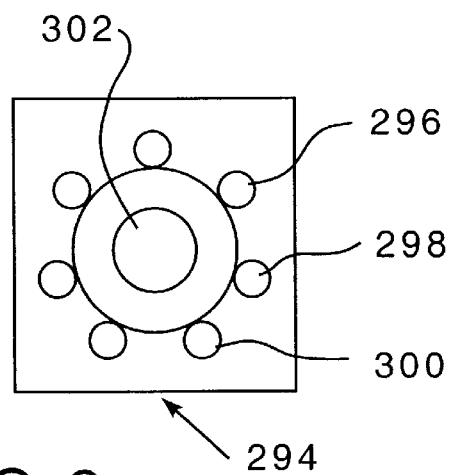
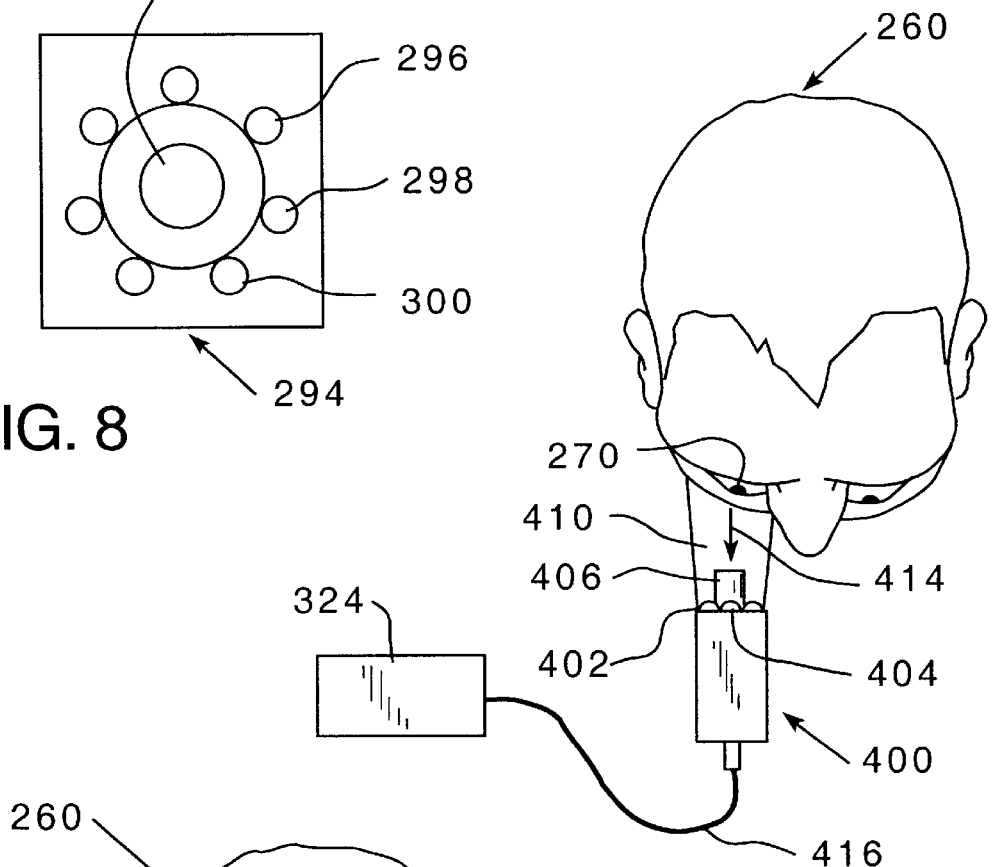
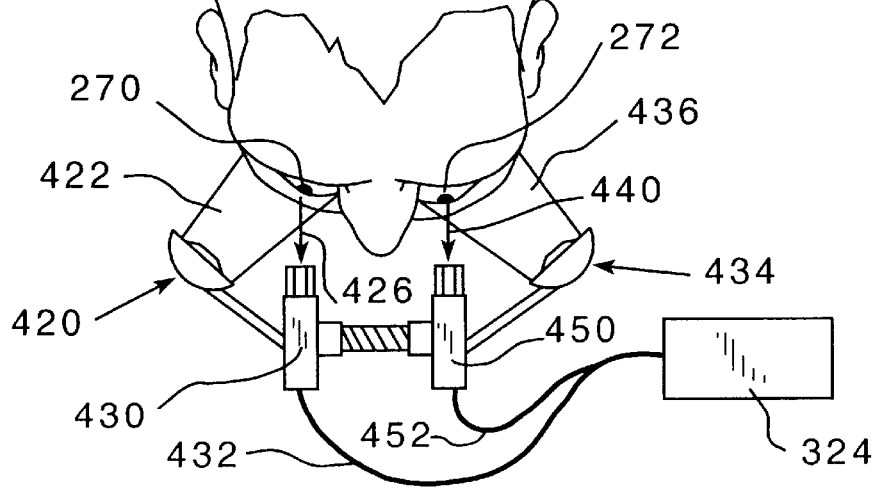

NON-INVASIVE OCULAR ASSESSMENT METHOD AND ASSOCIATED APPARATUS

CROSS-REFERENCE TO RELATED APPLICATION

The present application is a continuation-in-part of U.S. patent application Ser. No. 09/860,241 filed on May 18, 2001.

BACKGROUND OF THE INVENTION

1. Field of the Invention

The present invention relates to a method of ocular assessment to determine on an essentially real time basis certain physical conditions in the body and to apparatus for effecting such monitoring.

2. Description of the Prior Art

It has long been known to examine the eye to determine certain characteristics of the eye, such as near and far vision in order to ascertain whether an individual might need to wear corrective lenses in the form of eyeglasses or contact lenses, for example.

It has also been known to monitor the eye to determine other physical characteristics of the eye, such as the shape of the cornea. See, for example, U.S. Pat. Nos. 4,995,716 and 5,159,361.

U.S. Pat. No. 4,995,716 discloses apparatus for measuring the topography of a cornea. Light projection means projects a grid pattern on the eye which is coated with a substance capable of making the eye non-transparent. An electronic camera is provided in a second pathway in line with the eye for obtaining and producing an image of the grid pattern projected onto the eye. One arm of the apparatus carries the light projection means and the grid means on one side of the centerline and the camera means on the other side. Processing means are connected to the camera for obtaining data from the image of the grid pattern projected onto the eye thereby producing quantitative and qualitative analysis of the contour of the cornea. See, also, U.S. Pat. No. 5,159,361.

In summary, it has been known to provide apparatus to which non-contacting optical and electronic apparatus can make certain determinations about the eye itself as well as other conditions in the body as a result of changes in the eye.

In spite of the foregoing, there remains a real and substantial need for a method and associated apparatus for effecting automated determinations regarding certain specific conditions in the body based upon examination of the eye.

SUMMARY OF THE INVENTION

The present invention has met the above-described needs.

The present invention has provided a method of monitoring a medical condition in a subject. The method includes impinging light on to the subject's eye and directing the reflected light from the impinging light beam to a photosensor with subsequent conversion in the photosensor of the reflected light into corresponding electrical signals. The electrical signals are delivered to a processor, which may be a computer, which contains stored information regarding desired parameters of the particular medical condition. A comparison is effected between the photosensor delivered electrical signal containing the data and the stored data to determine if an undesirable medical condition exists and, if such an undesirable medical condition exists, communicating such event. The process is repeated cyclically. Among the specific conditions that may be monitored are miosis, carbon monoxide and other toxin levels in the body, and blood flow characteristics, for example.

The apparatus for monitoring a medical condition may have a light source directing light onto at least one eye of the subject with sensor means for receiving the reflected light and converting light into corresponding electrical signals. Processor means receive the electrical signals and compare the same with stored information regarding desired parameters of the medical condition and emits the result of the comparison. The processor has controls for cyclically repeating the monitoring at desired predetermined intervals.

It is an object of the present invention to provide an efficient and accurate means of employing information obtained from the eye to determine whether certain changes in the physical condition of an individual have occurred.

It is a further object of the present invention to effect such determinations rapidly in minimum time.

It is yet another object of the present invention to provide apparatus for making such determinations in vehicles, customized head mounted apparel at workstations and other ways which facilitate ongoing monitoring of the eye without interfering meaningfully with activities of the individual being monitored.

It is yet a further object of the present invention to provide such a method and apparatus which employs computerized processing through comparison of the data obtained from observations of the eye with either prior data obtained from the same individual or standardized data regarding normal and/or abnormal conditions in the body.

It is another object of the invention to provide an automated system for continuous or intermittent monitoring of some optically apparent characteristic that corresponds to an undesirable metabolic state or to a toxic exposure.

It is yet another object of the present invention to provide a system which serves as an early warning or generalized information leading to subsequent medical analysis.

It is yet another object of the invention to provide such a system which permits frequent monitoring of certain medical conditions as determined from external observation of the eye in order to minimize safety and health risks.

These and other objects of the invention will be more fully understood from the following description of the invention with reference to the drawings appended hereto.

BRIEF DESCRIPTION OF THE DRAWINGS

FIG. 8 is a front elevational view of a combination light source and camera employable in the present invention.

FIG. 9 is a top plan view, illustrating conceptionally the use of a combination light and lens on a single eye.

FIG. 10 is a top plan view illustrating a modified form of apparatus of the present invention, having separate light sources and sensors.

DESCRIPTION OF THE PREFERRED EMBODIMENTS

As employed herein, the term "subject" refers to human beings and other members of the animal kingdom unless in a specific usage an express indication to the contrary is provided.

As employed herein, "medical condition" means a condition of the body (other than direct measurement of vision) which condition can be determined through (a) monitoring of the condition of the eye or portions thereof (b) or changes in the condition of the eye or portions thereof and shall expressly include, but not be limited monitoring the amount of carbon monoxide and other toxic substances including but not limited to heavy metals, neurotoxins, organophosphates, fertilizers and pesticides.

The health and function of the eye reflects the general health of the body. The neural retina and optic nerve are extensions of the central nervous system. As a result, agents, which have general neurotoxic effects, will often affect the retina and optic nerve as well. The eye is supplied with blood by the ocular vasculature, which are visible through the front of the eye. Generalized diseases that affect the cardiovascular system are reflected in changes in these ocular vessels. Fluids in the eye interact with the lymphatic system of the body. Many chemicals and metals which enter the body, are transported by the vascular or lymphatic systems and are deposited in the eye. The cornea is an extremely sensitive ectodermal tissue that is sensitive to many of the same agents that affect the skin.

The method and apparatus of the present invention may be used in conjunction with a "dye" or other chemical injected into the blood stream or applied to the surface of the eye or its surrounding tissues. This dye or chemical might then react with a toxin and fluoresce or change color. The changes in the dye in time through the blood stream or on the surface of the eye or tissue surrounding the eye could provide indications of the presence of toxins or the health of vasculature and tissue or the accumulation of chemicals on or in vessels or tissues. Examples of this include, but are not limited to, current uses of fluorescein or other chemicals applied to the surface of the eye or orbit or injected to reveal vessels of the eye, retina, pupil and other ocular tissues. The system might monitor these changes statically or dynamically on the externally visible portions of the eye and its surrounding tissues or within the eye.

Figure 1:
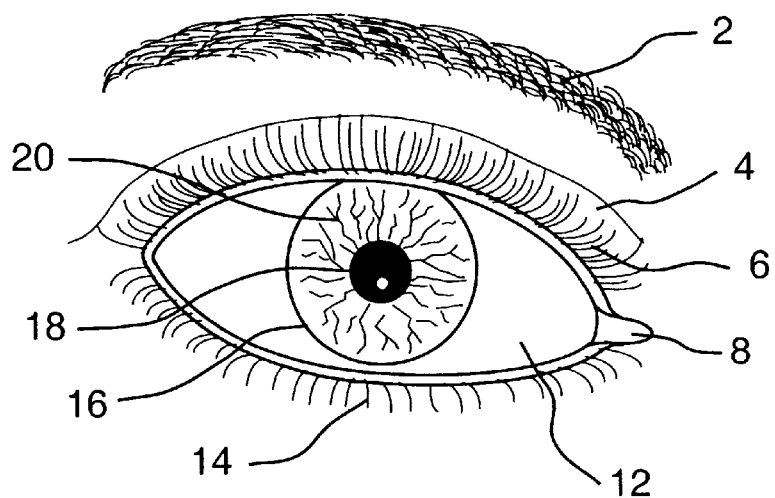
FIG. 1 is a schematic illustration of the human eye viewed from the exterior.

Referring to FIG. 1, there is shown an exterior view of a human eye which consists of an eyebrow 2, an upper eyelid 4, and eyelash 6 on the upper lid 4, a lacrimal duct 8, the white portion or sclera 12, a lower eyelid 14, an iris 16, a pupil 18, which is an opening in the iris 16, and the cornea 20.

Figure 2:
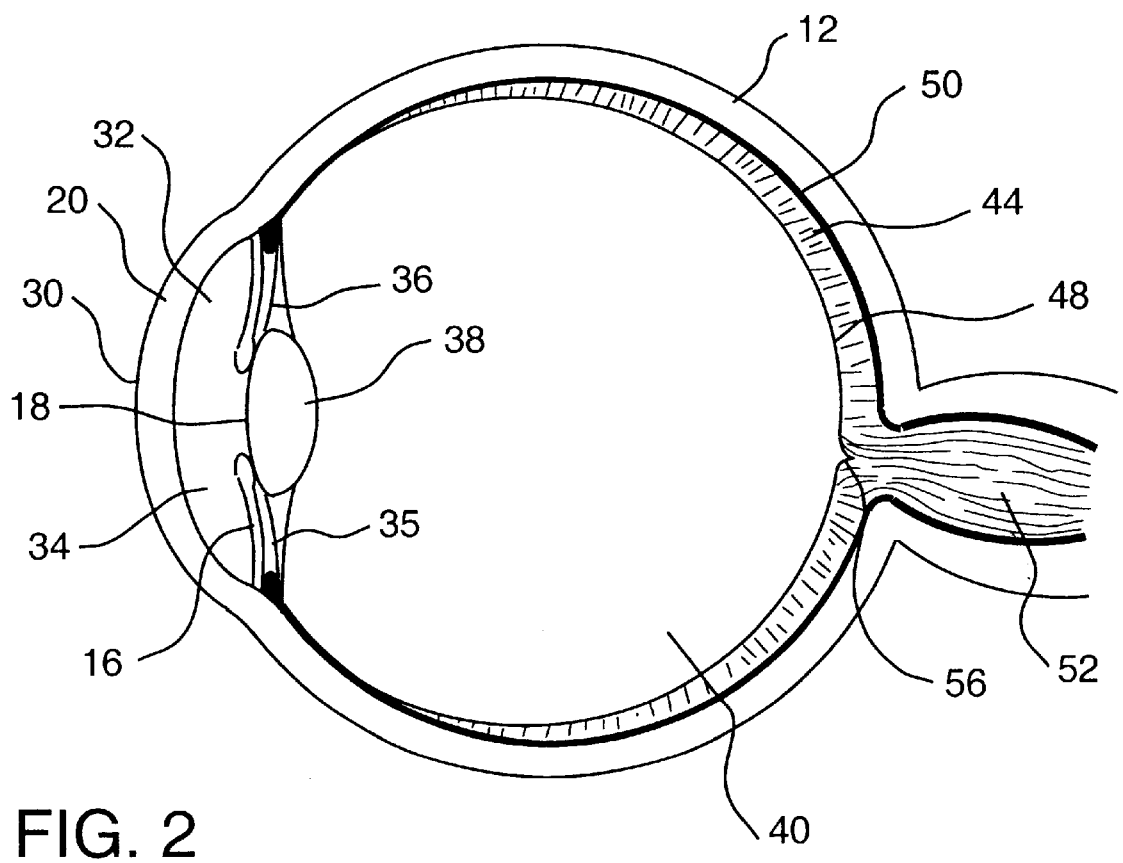
FIG. 2 is a schematic cross-section of the human eyeball.

FIG. 2 illustrates a cross-section of the human eyeball with the portion exposed to the exterior of the person appearing at the left where the conjunctiva 30 is located. An anterior chamber 32 and aqueous humor 34 are provided in the forefront. The suspensory ligament 36 is operatively associated with the lens 38. Other components of the eye are the vitreous body 40 which is disposed rearwardly of the lens 38 and forwardly of the retina 44 which has the fovea 48, optic nerve 52 and papilla 56 and choroid 50 positioned behind the same. The eye also contains the posterior chamber 35 and the ciliary process.

Light impinging upon the retina 44 in a particular pattern related to what the eye has observed is converted by the retina 44 into an electrical signal which is transmitted by the optic nerve 52 to the brain.

As will be described in greater detail hereinafter, where monitoring will occur at infrequent intervals in respect of a particular subject, apparatus suitable for receiving and supporting the subject's head so as to resist undesired movement may be combined with a structure supporting the light source and detectors which in turn are operatively associated with a processor. Where, however, ongoing monitoring on a continuous or frequent basis is contemplated, the invention should preferably be integrated into the subject's environment. Preferably, it would be integrated into a heads up display system, which while providing information to the subject would also permit monitoring of the subject's eye. Alternatively, the invention could be incorporated into the dashboard or visor or windshield of a vehicle with a zoomed view of the pilots/drivers eye.

Ambient illumination is preferred, but the heads up display could also serve as an illumination source. Alternatively, the system could be based on a non-visible wavelength of the electromagnetic spectrum, such as infrared viewing, either passively or actively illuminated.

An optics system could be employed for creating an image of the subject's eye on a sensor. Part of this system could be the light splitting system of a heads up display. The system could also employ a direct view of the area of interest without the use of an official interface such as in the use of a CCD chip, for example. The sensor is preferably a digital camera, but could be other types, such as video CCD cameras, CMOS devices, simple arrays of photo detectors, film, or others. The sensor can be selected to be sensitive to target portions of the light spectrum, however, simple gray scale cameras are probably adequate.

Filters can be utilized on the light beam reflected from the eye to further vary light spectrum selectivity. The miosis application, for example, does not require spectral measurements, but spectral filters may be utilized to minimize noise from the subject's environment or to filter out unwanted effects from the heads up display.

Focusing on a medical condition which involves determining if the subject is toxic one may look for a related biomarker. It is preferred to administer a toxin sensitive chemical substance which may be a dye or other chemical injected into the bloodstream or applied topically to the eye or its surrounding tissues. This dye or chemical would either enhance the biomarker or react with a specific toxin or toxins and would either fluoresce or change color or change in another manner or create changes perceived through the bloodstream or on the surface of the eye or surrounding tissue. This thereby provides a more tangible indication of the presence of an undesired toxin or toxins. These changes can be monitored on the eye and its surrounding tissues.

The stored information may consist of results of prior tests of the specific subject or general average information regarding the normal and abnormal toxic conditions. The stored information would also contain data regarding the nature of specific changes in the eye and how they relate to toxicity. This information will permit ready determination which correlates observed changes in the eye with toxicity and thereby enabling the monitoring process to make the desired determination.

A processor for analyzing images, preferably a computer, but also including custom designed circuits may be employed. This also requires the appropriate means of conveying the image from the sensor into the processor. In one form, this could consist of a high-speed digital bus. The processor would also in a manner well known to those skilled in the art have appropriate algorithms designed for isolation of information as to certain portions of the eye and measured characteristics thereof.

The results may then be communicated which could include radioing distress signals, vibratory output, audible tones, visual indicators or automatic changes in the system being operated. Also, CRT displays, hard copy output and storage in the processor may be provided with or without computer enhancement.

Figure 3:
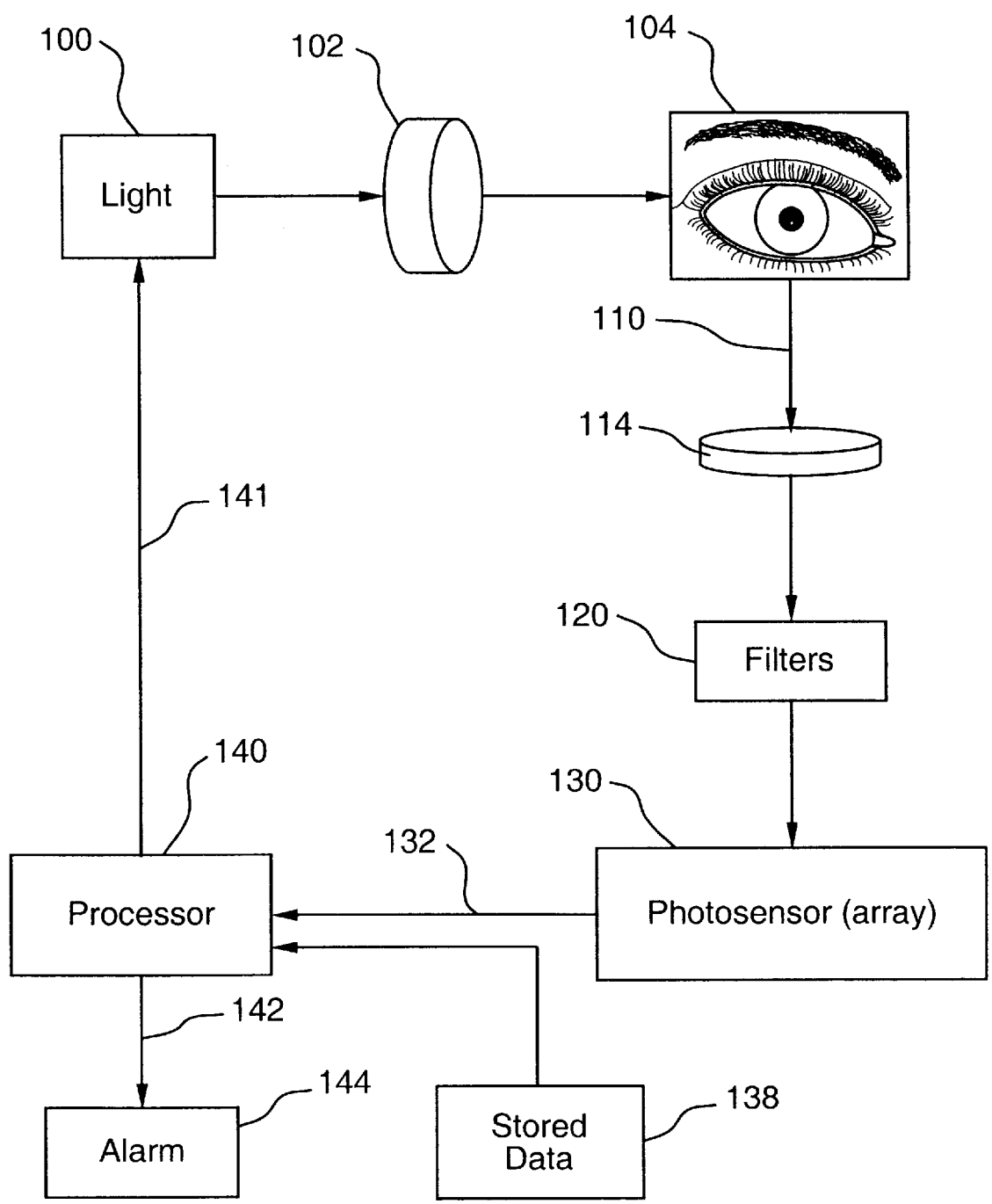
FIG. 3 is a flow diagram showing apparatus and a method of monitoring an individual.

Referring now to FIG. 3 a form of apparatus employable in a medical condition monitoring of the present invention will be considered. This embodiment may be employed, for example, to monitor toxins. A light source 100, which may be infrared light, emits light through optics 102 which may be an appropriate lens or lens system, causes the light to impinge upon a subject's eye 104. The reflected light 110 passes through optics 114, which may be a lens or lens system, through filter 120 to a sensor or sensor array 130 which may, for example, be a camera or a self-scanning array of photodiodes which responsive to the impinging light emits a corresponding electrical signal 132 to a processor 140 which processor 140 may be any suitable processor programmed to process the data received. Stored data 138 has been introduced into processor 140. This stored data may be subject's specific data previously obtained from the particular subject or data regarding normal and abnormal toxic conditions as well as eye changes resulting from such toxicity. Processor 140 through lead 141 controls the frequency of cycle initiation by controlling light 100. In a preferred embodiment of the invention, the microprocessor 140, which may be a computer or an intelligent chip, will have or stored therein or have access to a desired normal range of data which may either be that obtained from a general population source or in certain instances data obtained from the particular individual. When the data acquired departs from the desired range by a predetermined amount, the processor 140 may, for example, emit a signal 142 to an alarm 144 the alarm may take the form of an audible alarm, a visual alarm or a vibratory output which provides tactile feedback or a combination of these and other alarms. They may alert the individual being monitored or another to an undesired condition such as the onset of sleep or intoxication or reactions to drugs, including pharmaceutical and over-the-counter drugs, as well as illegal narcotics. This provides an opportunity for the individual to be spared from undesired consequences of one or more of these conditions or others. The information may then be delivered to a medical professional for appropriate treatment of the subject and if appropriate modification of the conditions that resulted in toxic exposure.

The present invention may also take advantage of the fact that many toxins have common biomarkers which tend to group together. For example, neuro-toxins tend to be similar to each other and heavy metals tend to be similar to each other. These characteristics serve to assist with the determination of relationships.

The preferred sensor is a system of one, two or more photosensors. The primary sensor should have optics gathering light for it from the sclera, or white of the eye, when the subject is looking in a prescribed direction (straight ahead, at a specific instrument or portion of a heads up display.) A second sensor could be utilized for measuring ambient light levels and associated measurement corrections. A third sensor could be positioned so that when the subject is looking in the prescribed direction (straight ahead), the low light reflectance corresponding to the dark pupil area of the eye could serve as a trigger to indicate that measurements of the white of the eye were valid.

Alternatively, the sensor could be the array of sensors of a digital camera where appropriate algorithms would determine where valid eye white measurements could be obtained. An algorithm for segmenting the sclera from a whole image could be a classic textbook segmentation algorithm or custom algorithms designed for pupil isolation. Also relative data between two parts of the eye may be compared such as data for the iris compared to data for the pupil. Also, measurements of both the external and internal portions of the eye may be employed.

Filters can be utilized to further vary light spectrum selectivity to the red portion of the spectrum.

A means for analyzing sensor data, preferably a custom circuit, but also including general microprocessors may be employed. This also employs appropriate means of conveying the sensor data from the sensor into the processor. In a preferred embodiment, this would consist of a set of digitized voltages. The processor could be placed in close proximity to the sensor or, if desired, be remotely located with wired or wireless communication between the processor and sensors and related components.

A means of correcting the measurement for ambient light variations may be provided in the processor.

A means of notifying someone of the results, could include radioing distress, audible tones for the subject, visual output, vibratory output or putting a vehicle into a "safe" mode of operation.

As in each of the processes, if desired, in addition to issuing or not issuing an alarm, a computer stored record of the inspection cycles with or without enhancement and with or without hard copy output or visual display on a monitor may be employed.

Figure 4:
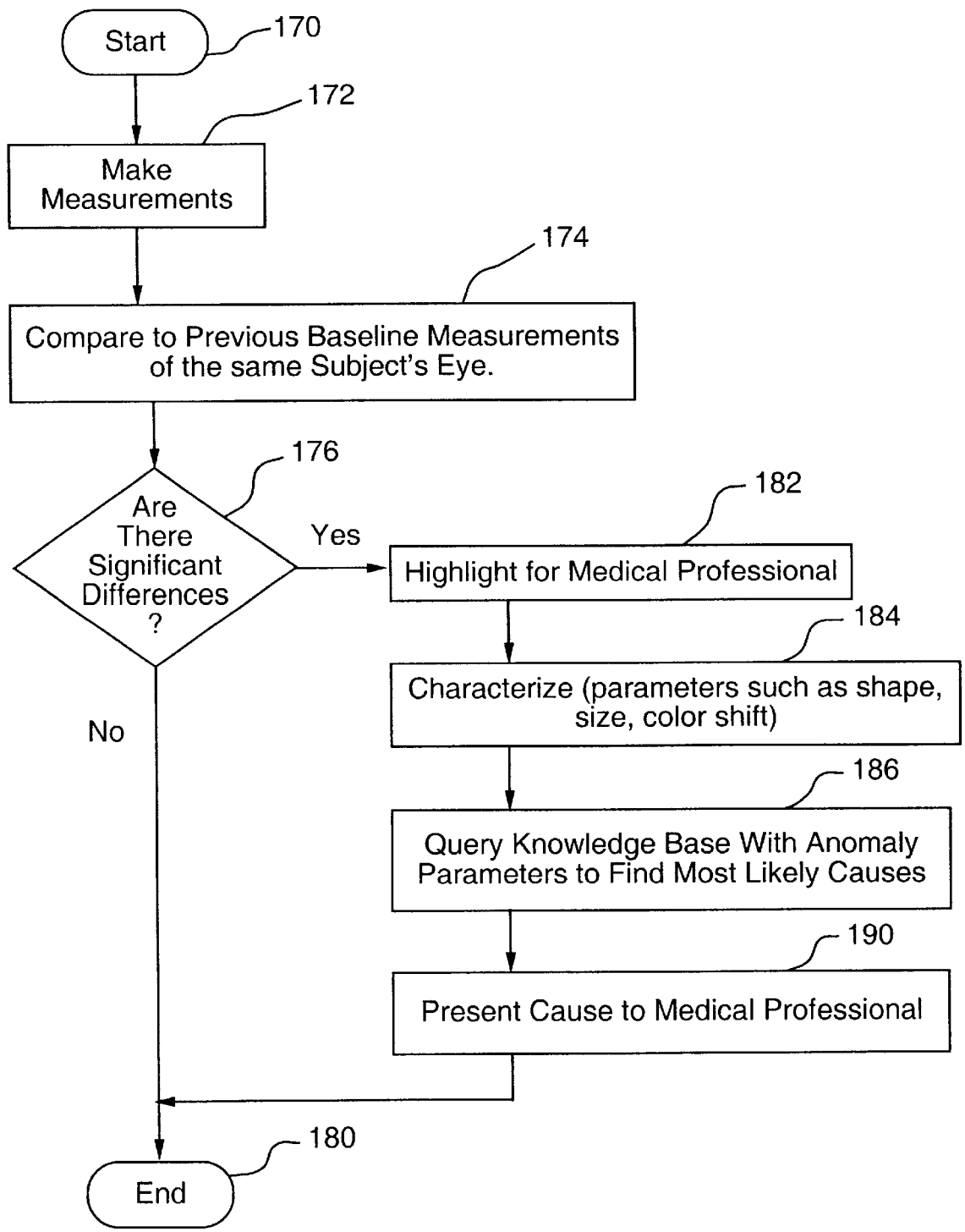
FIG. 4 is a schematic flow diagram showing one form of information processing information employed in the present invention.

Referring now again to FIG. 4, the flow chart of a form of process of the present invention will be considered. In effecting monitoring for medical conditions related to toxicity such as might be encountered for example in industrial exposure to elements toxic to the subject, such as for example lead or mercury, periodic tests will normally be run with a comparison being made between current measurements and stored information related to the particular subject and the particular toxin or toxins. As shown in FIG. 4, the start 170 of the process involves making of measurements 172 and comparing 174 the measurements with the baseline measurements contained in the stored information of the same subject's eye or eyes. A logic choice 176 is then made. If there are no significant differences, the test goes to the end 180. If there are significant differences, the differences are highlighted for medical professional 182 and may be characterized 184 according to changes in the eye such as shape, size, color, fluorescence and any other bio-markers which will in the processor be compared with existing data correlating such changes with levels of toxicity. This comparison 186 determines the cause or most likely cause which is presented 190 to the medical professional or others involved in the process. In this approach, the testing is normally performed at prolonged intervals as defined herein with corresponding changes being made in the subject's exposure to the toxic material if toxicity to one or more elements is determined to exist.

Figure 5:
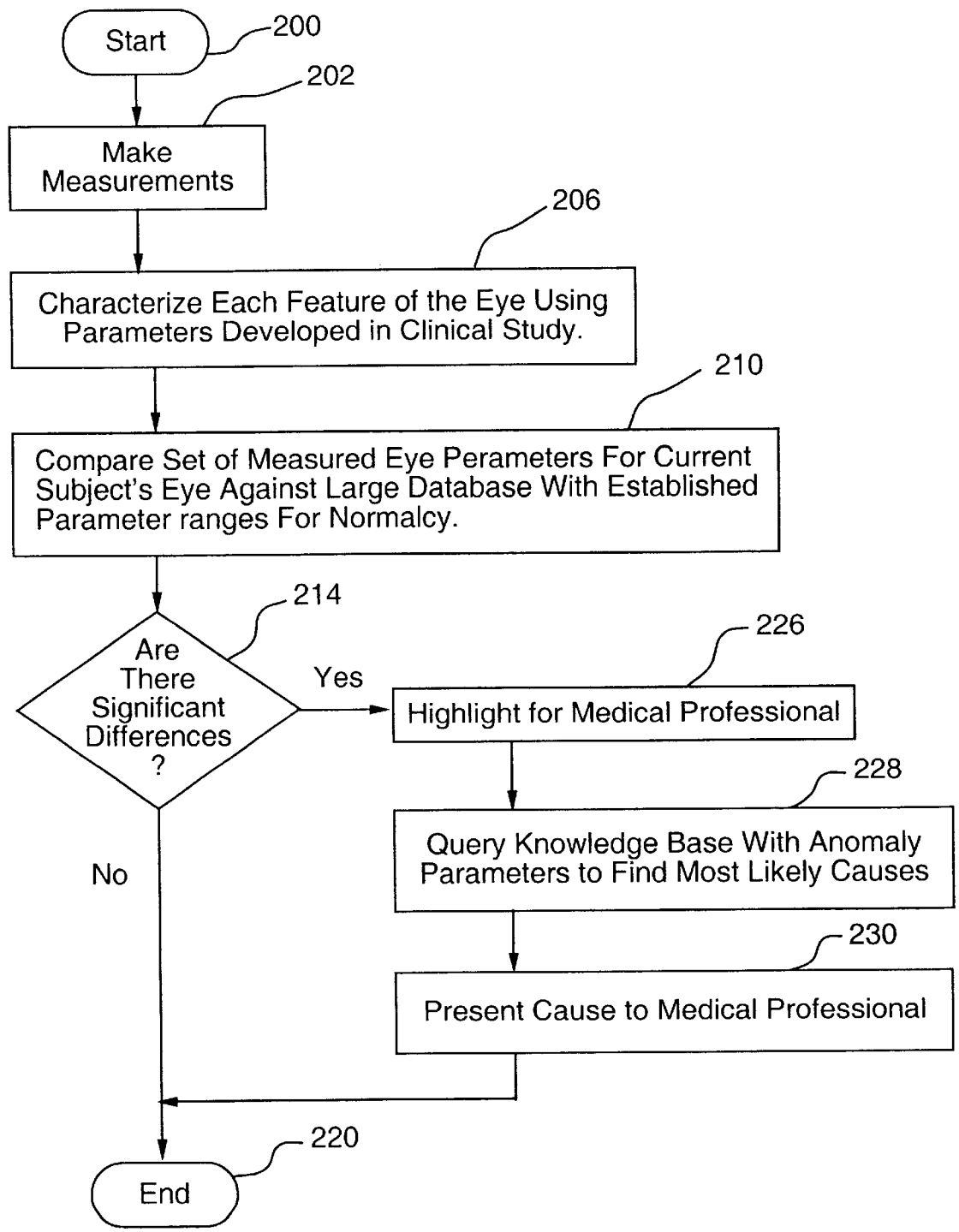
FIG. 5 is a schematic of a modified form of method of processing information of the present invention.

In an alternate form of the method of the present invention with reference to FIG. 5, the database will contain a large amount of information regarding normal levels of various toxins for purposes of comparison with the measurements on the subject. An alternate approach would be to have a smart system wherein a set of heuristic rules were created on the basis of the database information and are employed. Also stored would be information regarding normal and abnormal bio-markers such that the determined eye conditions can be correlated with a normal and acceptable toxicity level or an unacceptable one.

Referring FIG. 5, it is seen at the start 200 that measurements are made 202 with the stored information in the nature of normal and abnormal parameters determined from clinical studies 206 being employed. The database information regarding various conditions of the eye being monitored and how they correlate to the normal parameters is made 210. A logic decision 214 then results in the absence of a departure from normalcy indicating the end 220 of the test. If there is a meaningful departure, this information is provided to a medical professional 226. Departures from desired eye structure or conditions are then compared in the processor with various anomaly parameters 228 with the cause 230 being presented to the medical professional.

It will be appreciated that depending upon the nature of the testing done and the equipment available the subject's eyes may be monitored sequentially or simultaneously.

Figure 6:
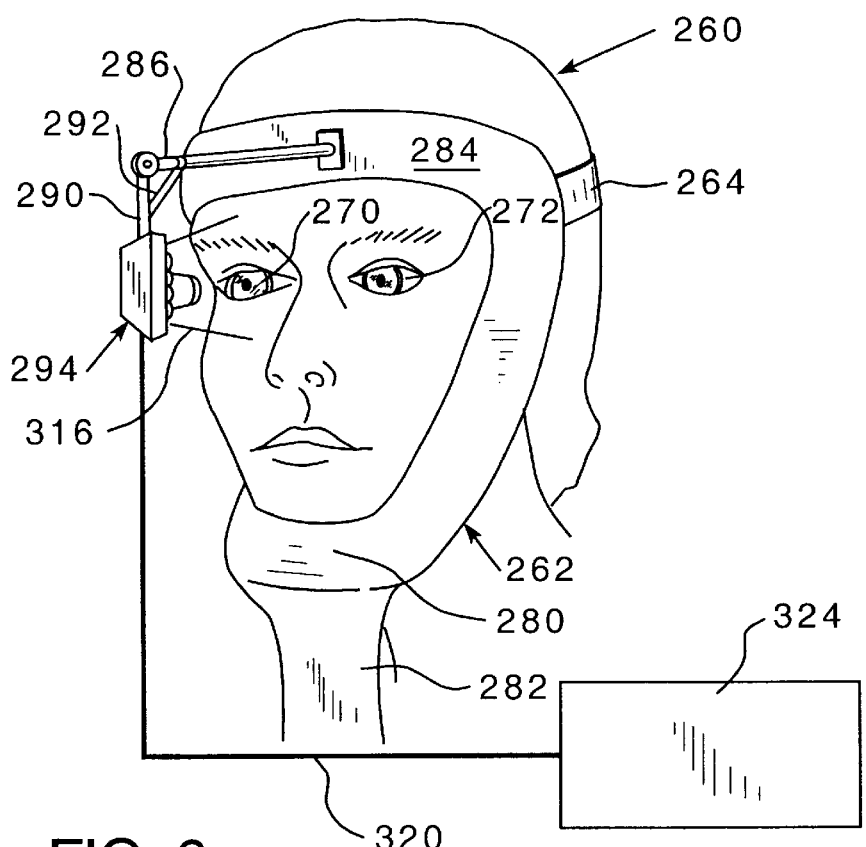
FIG. 6 is a schematic view of a form of apparatus employed to examine a single eye at a time.

Referring to FIG. 6, there is shown, schematically a subject 260 which is a human being, wearing a mask 262, which is secured to the individual by a strap 264 and defined an opening through which a major portion of the face and, specifically, the eyes 270, 272 are exposed. Integral with the mask 262 is a lower chin support portion 280, which in turn is supported by a suitable post 282, which may be anchored to any suitable base (not shown). Supported by the upper mask portion 284 by means of a strut member 286, and a depending arm 290, with a reinforcing angle brace 292 is a combination light source and sensor 294. Referring to FIG. 8, there is shown the combination light source and sensor, which has a plurality, circumferentially spaced light sources 296, 298, 300, for example, and a centrally located camera 302.

In operation of this embodiment of the system, the light source and lens combination 294 will be employed to examine eye 270 with a plurality of light beams 310 fully illuminating eye 270, and reflected light being received in camera 302, which converts the received light into an output electrical signal corresponding thereto over line 320 to processor 324 wherein stored data, relating to various eye conditions is provided, and a comparison with the data received is made. The system otherwise may function in the manner hereinbefore described.

Figure 7:
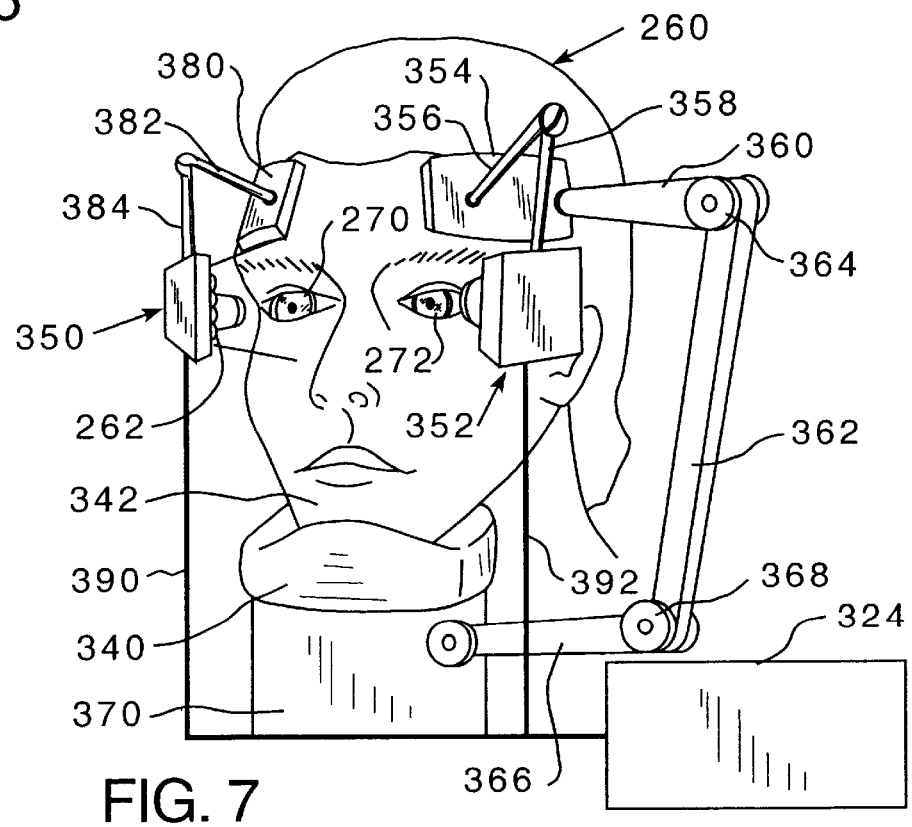
FIG. 7 is a schematic view similar to FIG. 6, except showing apparatus which is adapted to be employed in inspecting both eyes either sequentially or simultaneously and showing modified apparatus support structure.

Referring to FIG. 7, the individual 260 has a chin support 340 supporting the chin 342 with a pair of systems adapted to examine, respectively, each eye 270 and eye 272. A pair of combination light sources and cameras 350, 352 may each be provided with a plurality of light sources and a camera and as exemplified by 352 may be supported by an anchor plate 354 and appropriate linkage 356, 358 with a suitable adjustment linkage assembly 360 connected to arm 362 by articulating connector 364, which further may be connected to arm 366 through articulating connector 368 which, in turn, may be secured to support column 370. A similar support linkage may be provided for a combination light source and lens 350, which has anchor plate 380 and linkage elements 382, 384 supporting the combination light source and lens 350. It will be appreciated that with this embodiment, the output of combination light source and lens 350 will be provided over lead 390 to processor 324 and the output of combination light source and camera 352 will be provided over lead 392 to processor 324. In this embodiment, both eye 270, 272 may be examined sequentially under the control of processor 324 or simultaneously, if desired. In the embodiments of FIG. 6 and 7, the operation of the light source may be controlled by processor 324 in a manner well-known to those skilled in the art.

Referring to FIG. 9, this figure shows a top plan view of a human subject 260 wherein the combination light source and camera 400, has a plurality of light sources 402, 404 for example and a camera having a forwardly projecting camera lens 406, with the combined beam of light 410 impinging on eye 270 and the reflected light 414 indicated generally by an arrow entering camera 406. The electrical output of the light source camera, unit 400, is passed over lead 416 to processor 324.

With reference to FIG. 10, there is shown a subject 260 and a modified embodiment of the invention. In this embodiment of the invention, which is structured to provide analysis for both eyes 270, 272, and the first light source 420 creates a light beam 422 which impinges on eye 270 with the resultant reflected light as represented by arrow 426 being received in camera 430, which in turn converts the received light into corresponding electrical signal which passes over lead 432 to processor 324. Similarly, second light source 434 creates a light beam 436 which impinges on eye 272 and, as indicated by arrow 440, causes reflected light to enter camera 450 which converts the received light into corresponding electrical signals, which pass over lead 452 to processor 324.

Figure 11:
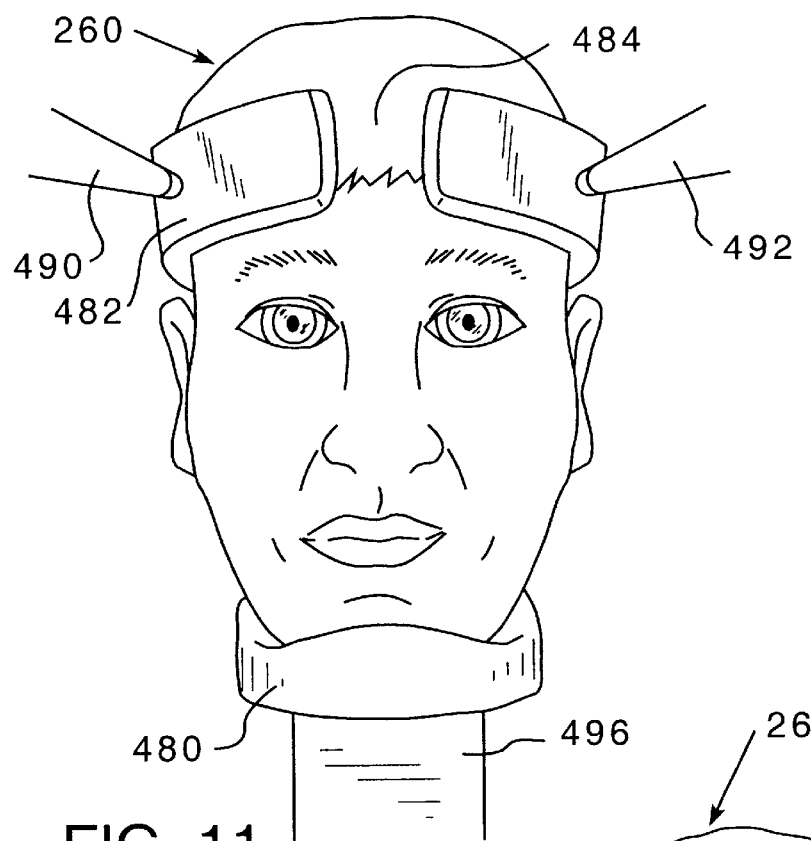
FIG. 11 is a front elevational view showing a form of head-restraint usable in the present invention.

FIG. 11 illustrates a modified form of restraint, which includes a chin support 480, supporting post 496 and a broken band 482 which has a gap 484 and a positioning element 490, 492 secured thereto.

Figure 12:
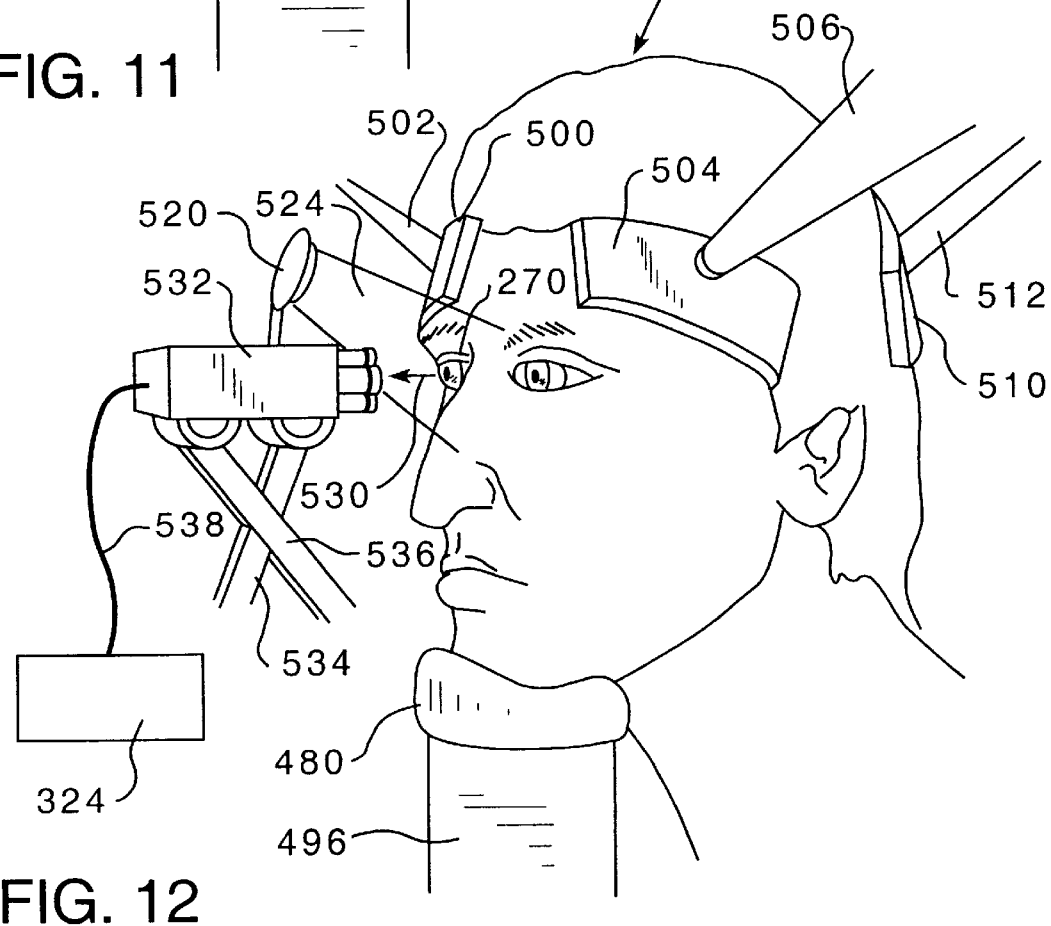
FIG. 12 is a schematic prospective view of a form of apparatus showing head restraint and light source and associated and sensing and processing apparatus.

FIG. 12 shows a chin support 480 supporting the chin of subject 260 with an underlying support post 496. Rather than having a discontinuous band supporting the upper head portion, in this embodiment, a first support member 500, which is secured to a support arm 502 and a second support member 504, which is secured to a second support arm 506, cover only a portion of the subject's head and a rear support 510, which is secured to a support arm 512, serves to immobilize the subject's head. The light source 520, impinges a light beam 524 on eye 270 with reflected light as represented by arrow 530 being received within camera 532 which is provided with adjustable supports 534, 536 and provides output over lead 538 to processor 324.

If desired, additional restraints such as one contacting the rear of the head and the forehead, for example, (not shown) may be employed if desired. In this manner, inaccuracies in monitoring due to head movement will be reduced or substantially completely eliminated. The processor will generally be programmed to confirm that the eye is in the desired position before processing the data received.

With respect to particular monitoring support and positions for the apparatus of the present invention numerous modes of energizing and communicating with the same will be known to those skilled in the art. To the extent to which that it is to be mounted on head supporting apparatus, the system and a source of energizing the same may all be contained within the head supporting apparatus with a suitable means for monitoring at least one eye of the user. Mounting such a system in the user environment has been disclosed, for example, in the product offered by Iscan, Inc. of Burlington, Me. under the general trade designation "HEADHUNTER." Devices may also be mounted in vehicles or in regions adjacent to where the individual will be positioned.

It will be appreciated that for short interval monitoring, it will generally be preferred to have at least one eye of the individual monitored by the system at frequent predetermined intervals. The frequency of such monitoring will depend to a great extent upon the nature of the activity, the purpose for which monitoring is being initiated, the nature of the characteristic being involved, the degree of the potential health or safety hazard involved, as well as other factors. For miosis and carbon monoxide, it will generally involve a monitoring cycle occurring about every 1/60 to 30 seconds and preferably about every 1/2 to 10 seconds. This provides not only frequent data, but also facilitates monitoring trends.

It will be appreciated that the invention may also be employed advantageously to provide for periodic monitoring of patients at intervals of days, weeks, months or years for comparison purposes in order to determine if meaningful changes have occurred over time. For convenience of reference herein, in order to distinguish these longer periods of time from the shorter repeated cycles which may be about 1/60 to 30 seconds between cycles, such longer periods between monitored cycles will be referred to as "prolonged intervals", and the shorter intervals of less than one hour, will be referred to as "short intervals".

It will be appreciated from the foregoing that various monitoring functions with respect to the eye not including checking of an individual's vision directly but rather employing the conditions of the eyes as an indication of the presence or absence of toxicity or other conditions within the subject may be employed. For example, visible light images of the retina including nerves and vasculature may be obtained. Spectrally filtered images of the retina including the typical red-green-blue color, an array of discrete spectral images and special filters for highlighting known sources of aberrations indicative of specific afflictions may be employed. Further, these items may be expanded beyond the visible spectrum into non-visible regions of the spectrum. The lighting which is employed will be so designed so as to facilitate structural measurements of various eye components such as the lens, for example. Further, dyes or other toxin sensitive chemical elements may be employed in order to enhance determination of anomalies.

It will be appreciated from the foregoing that the present invention provides an effective means for monitoring of medical conditions so as to provide indications of potentially hazardous conditions with primary emphasis on toxicity from a number of sources.

While for convenience of disclosure herein reference has been made to the human eye, in certain instances advantageous use of the invention may be made on animals, such as guard dogs, livestock, fish, working animals, or wildlife, for example. All of this has been accomplished in an economical, simple and efficient automated manner.

Whereas particular embodiments of the invention have been described herein for purposes of illustration, it will be evident to those skilled in the art that numerous variations of the details may be made without departing from the invention as defined in the appended claims.

We claim:

1. A method of monitoring a medical condition including a toxin in a subject comprising administering a chemical substance to said subject, impinging light on a subject's eye, directing reflected light from said impinging light beam to a photosensor, converting said reflected light into corresponding electrical signals, delivering said electrical signals to a processor which contains stored information regarding desired parameters for the particular medical condition including a biomarker related to said toxin, and effecting a comparison between the photosensor delivered electrical signals and the stored information to determine if an undesirable medical condition exists and if such undesirable medical condition exists communicating such event.

2. The method of claim 1 including cyclically repeating said method.

3. The method of claim 2 including repeating said method after a prolonged interval.

4. The method of claim 2 including employing optics to direct said reflected light beam to said eye and employing optics to direct said reflected light to said photosensor.

5. The method of claim 4 including filtering the reflected light emerging from said optics prior to introducing said light beam into said photosensor.

6. The method of claim 1 including on the basis of said monitoring determining a likely toxic cause of said undesirable medical condition.

7. The method of claim 1 including stabilizing the subject's head to resist undesired motion thereof during said monitoring.

8. The method of claim 1 including monitoring each eye of said subject sequentially.

9. The method of claim 1 including monitoring both eyes of said subject substantially simultaneously.

10. The method of claim 1 including employing as said stored information average data relating to a medical condition as related to the general population.

11. The method of claim 1 including employing as said stored information data with respect to said toxin obtained from said subject.

12. The method of claim 1 including effecting said monitoring by employing as said stored information a set of heuristic rules developed from database information related to said medical condition.

13. A method of monitoring a medical condition in a subject comprising administering a chemical substance to said subject, impinging light on a subject's eye, directing reflected light from said impinging light beam to a photosensor, converting said reflected light into corresponding electrical signals, delivering said electrical signals to a processor which contains stored information regarding desired parameters for the particular medical condition, effecting a comparison between the photosensor delivered electrical signals and the stored information to determine if an undesirable medical condition exists and if such undesirable medical condition exists communicating such event, employing a toxin sensitive chemical substance as said chemical substance, and administering said toxin sensitive chemical substance by injection.

14. A method of monitoring a medical condition in a subject comprising administering a chemical substance to said subject, impinging light on a subject's eye, directing reflected light from said impinging light beam to a photosensor, converting said reflected light into corresponding electrical signals, delivering said electrical signals to a processor which contains stored information regarding desired parameters for the particular medical condition, effecting a comparison between the photosensor delivered electrical signals and the stored information to determine if an undesirable medical condition exists and if such undesirable medical condition exists communicating such event, employing a toxin sensitive chemical substance as said chemical substance, and administering said toxin sensitive chemical substance topically to the surface of the eye or its surrounding tissues.

15. A method of monitoring a medical condition in a subject comprising administering a chemical substance to said subject, impinging light on a subject's eye, directing reflected light from said impinging light beam to a photosensor, converting said reflected light into corresponding electrical signals, delivering said electrical signals to a processor which contains stored information regarding desired parameters for the particular medical condition, effecting a comparison between the photosensor delivered electrical signals and the stored information to determine if an undesirable medical condition exists and if such undesirable medical condition exists communicating such event, on the basis of said monitoring determining a likely toxic cause of said undesirable medical condition, employing a toxin-sensitive chemical substance as said chemical substance, and said toxin sensitive chemical substance responsive to the existence of a predetermined level of said toxin will effect a visually perceptible change in the eye so as to permit said determination to be made.

16. A method of monitoring a medical condition in a subject comprising administering a chemical substance to said subject, impinging light on a subject's eye, directing reflected light from said impinging light beam to a photosensor, converting said reflected light into corresponding electrical signals, delivering said electrical signals to a processor which contains stored information regarding desired parameters for the particular medical condition, effecting a comparison between the photosensor delivered electrical signals and the stored information to determine if an undesirable medical condition exists and if such undesirable medical condition exists communicating such event, and employing fluorescein as said chemical substance.

17. Apparatus for monitoring a medical condition including a toxin in a subject comprising a light source for directing light onto at least one eye of said subject, sensor means for receiving reflected light from said eye and converting said light into corresponding electrical signals, a processor for receiving said electrical signals, said processor having stored information regarding desired parameters of said medical condition including a biomarker related to said toxin, and said processor having the capability of effecting a comparison of information obtained from said electric signals with said stored information and emitting a determination of said comparison as to whether said medical condition exists or not.

18. The apparatus of claim 17 including said processor having controls for cyclically repeating said monitoring at predetermined intervals.

19. The apparatus of claim 18 including said processor having the capability of repeating said process at prolonged intervals.

20. The apparatus of claim 17 including employing as said stored information information previously obtained from said subject.

21. The apparatus of claim 17 including employing as said stored information information obtained from sources other than said subject.

22. The apparatus of claim 17 including support for said subject's head to resist undesired movement thereof during use of said apparatus.

23. The apparatus of clam 22 including said support including a chin support and at least one head restraint.

24. The apparatus of claim 17 including said apparatus being structured to monitor each eye sequentially.

25. The apparatus of claim 17 including said apparatus being structured to monitor both eyes simultaneously.

26. The apparatus of claim 17 including an alarm being activatable when an undesired medical condition exists through a predetermined amount of carbon monoxide being present in the subject.

27. The apparatus of claim 17 including said stored information including information regarding normal eyes and eyes of subjects experiencing adverse consequences of toxicity.

28. The apparatus of claim 17 including first optics for directing said light beam to said eye and second optics for directing said reflected light to said photosensors.

29. The apparatus of claim 28 including a light filter for filtering the reflected light emerging from said second optics prior to introducing said light beam into said photosensors.

30. The apparatus of claim 17 including said light source having a first light source for one eye and a second light source for the other eye.

31. The apparatus of claim 17 including said light source having a plurality of lights surrounding said sensor means.

32. The apparatus of claim 17 including said light source structured to emit a light beam that is spaced from said sensor means.

33. Apparatus for monitoring a medical condition in a subject comprising a light source for directing light onto at least one eye of said subject, sensor means for receiving reflected light from said eye and converting said light into corresponding electrical signals, a processor for receiving said electrical signals, said processor having stored information regarding desired parameters of said medical condition, said processor having the capability of effecting a comparison of information obtained from said electric signals with said stored information and emitting a determination of said comparison as to whether said medical condition exists or not, and said stored information including information regarding toxic thresholds of at least one material selected from the group consisting of heavy metals, neurotoxins, organophosphates, fertilizers and pesticides and changes in the eye created by exceeding one more of said thresholds.

34. The apparatus of claim 33 including said stored information including information regarding toxin sensitive chemical substances and related changes in the eye resulting from administering the same to the subject.

35. The apparatus of claim 33 including said support supporting said light source and said sensor means.

* * * * *

UNITED STATES PATENT AND TRADEMARK OFFICE
CERTIFICATE OF CORRECTION

PATENT NO. : 6,631,989 B2
DATED : October 14, 2003
INVENTOR(S) : James V. Odom et al.

It is certified that error appears in the above-identified patent and that said Letters Patent is hereby corrected as shown below:

<u>Column 12,</u>
Line 39, "clam" should read -- claim --.

<u>Column 13,</u>
Line 1, insert a new paragraph after "including".

Signed and Sealed this

Thirtieth Day of March, 2004

JON W. DUDAS
*Acting Director of the United States Patent and Trademark Office*